United States Patent
Larson et al.

(10) Patent No.: US 8,206,372 B2
(45) Date of Patent: Jun. 26, 2012

(54) CATHETER WITH SPIRAL CUT TRANSITION MEMBER

(75) Inventors: Christopher R. Larson, St. Paul, MN (US); Angela Kornkven Volk, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/793,305

(22) Filed: Jun. 3, 2010

(65) Prior Publication Data

US 2010/0241154 A1    Sep. 23, 2010

Related U.S. Application Data

(60) Continuation of application No. 11/516,062, filed on Sep. 6, 2006, now Pat. No. 7,744,586, which is a continuation of application No. 10/285,948, filed on Nov. 1, 2002, now Pat. No. 7,115,183, which is a continuation of application No. 09/534,870, filed on Mar. 24, 2000, now Pat. No. 6,475,209, which is a division of application No. 09/241,995, filed on Feb. 2, 1999, now Pat. No. 6,048,338, which is a continuation-in-part of application No. 08/950,864, filed on Oct. 15, 1997, now Pat. No. 5,891,110.

(51) Int. Cl.
*A61M 25/00* (2006.01)
(52) U.S. Cl. ...................................................... 604/523
(58) Field of Classification Search .................... 604/523
See application file for complete search history.

(56) References Cited

U.S. PATENT DOCUMENTS

| | | |
|---|---|---|
| 3,911,927 A | 10/1975 | Rich et al. |
| 4,085,185 A | 4/1978 | Adair |
| 4,195,637 A | 4/1980 | Gruntzig et al. |
| 4,249,536 A | 2/1981 | Vega |
| 4,251,305 A | 2/1981 | Becker et al. |
| 4,307,722 A | 12/1981 | Evans |
| 4,323,071 A | 4/1982 | Simpson et al. |
| 4,385,635 A | 5/1983 | Ruiz |
| 4,413,989 A | 11/1983 | Schjeldahl et al. |
| 4,425,919 A | 1/1984 | Alston, Jr. et al. |

(Continued)

FOREIGN PATENT DOCUMENTS

EP    0171884    2/1986

(Continued)

OTHER PUBLICATIONS

Hawley's Condensed Chemical Dictionary, 1993, p. 873.

(Continued)

*Primary Examiner* — Nicholas Lucchesi
*Assistant Examiner* — Jason Flick
(74) *Attorney, Agent, or Firm* — Seager, Tufte & Wickhem, LLC

(57) ABSTRACT

A tubular transition member having an annular wall with at least one cut extending through the annular wall is disclosed for controlling a transition in stiffness of a catheter from a stiffer more pushable proximal section to a more flexible and trackable distal section and increasing kink resistance. The transition member may extend across the junction formed between the stiffer proximal section and the more flexible distal section. The transition member may be used in conjunction with any type of catheter including single-operator-exchange type catheters, over-the wire type catheters, and/or fixed-wire type catheters.

18 Claims, 2 Drawing Sheets

U.S. PATENT DOCUMENTS

| | | | |
|---|---|---|---|
| 4,456,000 A | 6/1984 | Schjeldahl et al. | |
| 4,490,421 A | 12/1984 | Levy | |
| 4,531,512 A | 7/1985 | Wolvek et al. | |
| 4,531,943 A | 7/1985 | Van Tassel et al. | |
| 4,540,404 A | 9/1985 | Wolvek | |
| 4,551,292 A | 11/1985 | Fletcher et al. | |
| 4,588,399 A | 5/1986 | Nebergall et al. | |
| 4,596,563 A | 6/1986 | Pande | |
| 4,636,272 A | 1/1987 | Riggs | |
| 4,636,346 A | 1/1987 | Gold et al. | |
| 4,646,719 A | 3/1987 | Neuman et al. | |
| 4,676,229 A | 6/1987 | Krasnicki et al. | |
| 4,706,670 A | 11/1987 | Andersen et al. | |
| 4,739,768 A | 4/1988 | Engelson | |
| 4,748,982 A | 6/1988 | Horzewski et al. | |
| 4,753,765 A | 6/1988 | Pande | |
| 4,759,748 A | 7/1988 | Reed | |
| 4,764,324 A | 8/1988 | Burnham | |
| 4,782,834 A | 11/1988 | Maguire et al. | |
| 4,808,164 A | 2/1989 | Hess | |
| 4,817,613 A | 4/1989 | Jaraczewski et al. | |
| 4,819,751 A | 4/1989 | Shimada et al. | |
| 4,820,349 A | 4/1989 | Saab | |
| 32,983 A | 7/1989 | Levy | |
| 4,863,442 A | 9/1989 | DeMello et al. | |
| 4,884,573 A | 12/1989 | Wijay et al. | |
| 4,886,506 A | 12/1989 | Lovgren et al. | |
| 33,166 A | 2/1990 | Samson | |
| 4,898,896 A | 2/1990 | Maj et al. | |
| 4,906,241 A | 3/1990 | Noddin et al. | |
| 4,906,244 A | 3/1990 | Pinchuk et al. | |
| 4,917,666 A | 4/1990 | Solar et al. | |
| 4,921,483 A | 5/1990 | Wijay et al. | |
| 4,943,278 A | 7/1990 | Euteneuer et al. | |
| 4,955,377 A | 9/1990 | Lennox et al. | |
| 4,955,862 A | 9/1990 | Sepetka | |
| 4,960,410 A | 10/1990 | Pinchuk | |
| 4,963,313 A | 10/1990 | Noddin et al. | |
| 4,964,409 A | 10/1990 | Tremulis | |
| 4,964,853 A | 10/1990 | Sugiyama et al. | |
| 4,976,720 A | 12/1990 | Machold et al. | |
| 4,994,018 A | 2/1991 | Saper | |
| 4,994,032 A | 2/1991 | Sugiyama et al. | |
| 33,561 A | 3/1991 | Levy | |
| 4,998,923 A | 3/1991 | Samson et al. | |
| 5,002,559 A | 3/1991 | Tower | |
| 5,047,045 A | 9/1991 | Arney et al. | |
| 5,050,606 A | 9/1991 | Tremulis | |
| 5,078,702 A | 1/1992 | Pomeranz | |
| 5,078,727 A | 1/1992 | Hannam et al. | |
| 5,087,394 A | 2/1992 | Keith | |
| 5,093,546 A | 3/1992 | Matsumiya et al. | |
| 5,100,381 A | 3/1992 | Burns | |
| 5,108,415 A | 4/1992 | Pinchuk et al. | |
| 5,120,308 A | 6/1992 | Hess | |
| 5,122,125 A | 6/1992 | Deuss | |
| 5,139,496 A | 8/1992 | Hed | |
| 5,143,093 A | 9/1992 | Sahota | |
| 5,147,377 A | 9/1992 | Sahota | |
| 5,154,725 A | 10/1992 | Leopold | |
| 5,156,594 A | 10/1992 | Keith | |
| 5,156,612 A | 10/1992 | Pinchuk et al. | |
| 5,158,548 A | 10/1992 | Lau et al. | |
| 5,159,937 A | 11/1992 | Tremulis | |
| 5,163,989 A | 11/1992 | Campbell et al. | |
| 5,171,230 A | 12/1992 | Eland et al. | |
| 5,176,637 A | 1/1993 | Sagae | |
| 5,180,585 A | 1/1993 | Jacobson et al. | |
| 5,209,728 A | 5/1993 | Kraus et al. | |
| 5,213,574 A | 5/1993 | Tucker | |
| 5,221,270 A | 6/1993 | Parker | |
| 5,226,888 A | 7/1993 | Arney | |
| 5,234,416 A | 8/1993 | Macaulay et al. | |
| 5,240,537 A | 8/1993 | Bodicky | |
| 5,254,091 A | 10/1993 | Aliahmad et al. | |
| 5,256,144 A | 10/1993 | Kraus et al. | |
| 5,256,145 A | 10/1993 | Atkinson et al. | |
| 5,258,160 A | 11/1993 | Utsumi et al. | |
| 5,259,839 A | 11/1993 | Burns | |
| 5,270,086 A | 12/1993 | Hamlin | |
| 5,279,561 A | 1/1994 | Roucher et al. | |
| 5,279,562 A | 1/1994 | Sirhan et al. | |
| 5,304,134 A | 4/1994 | Kraus et al. | |
| 5,304,198 A | 4/1994 | Samson | |
| 5,304,340 A | 4/1994 | Downey | |
| 5,316,706 A | 5/1994 | Muni et al. | |
| 5,318,032 A | 6/1994 | Lonsbury et al. | |
| 5,318,527 A | 6/1994 | Hyde et al. | |
| 5,318,532 A | 6/1994 | Frassica | |
| 5,324,259 A | 6/1994 | Taylor et al. | |
| 5,324,263 A | 6/1994 | Kraus et al. | |
| 5,328,468 A | 7/1994 | Kaneko et al. | |
| 5,334,146 A | 8/1994 | Ozasa | |
| 5,334,148 A | 8/1994 | Martin | |
| 5,334,168 A | 8/1994 | Hemmer | |
| 5,335,410 A | 8/1994 | Burnham | |
| 5,342,386 A | 8/1994 | Trotta | |
| 5,344,400 A | 9/1994 | Kaneko et al. | |
| 5,346,505 A | 9/1994 | Leopold | |
| 5,358,486 A | 10/1994 | Saab | |
| 5,358,493 A * | 10/1994 | Schweich et al. | 604/264 |
| 5,370,615 A | 12/1994 | Johnson | |
| 5,370,655 A | 12/1994 | Burns | |
| 5,387,193 A | 2/1995 | Miraki | |
| 5,389,087 A | 2/1995 | Miraki | |
| 5,395,334 A | 3/1995 | Keith et al. | |
| 5,397,306 A | 3/1995 | Nobuyoshi et al. | |
| 5,399,164 A | 3/1995 | Snoke et al. | |
| 5,403,292 A | 4/1995 | Ju | |
| 5,405,338 A | 4/1995 | Kranys | |
| 5,411,477 A | 5/1995 | Saab | |
| 5,415,635 A | 5/1995 | Bagaoisan et al. | |
| 5,423,754 A * | 6/1995 | Cornelius et al. | 604/103 |
| 5,425,709 A | 6/1995 | Gambale | |
| 5,425,712 A | 6/1995 | Goodin | |
| 5,443,495 A | 8/1995 | Buscemi et al. | |
| 5,447,497 A | 9/1995 | Sogard et al. | |
| 5,454,795 A | 10/1995 | Samson | |
| 5,458,613 A | 10/1995 | Gharibadeh et al. | |
| 5,470,313 A | 11/1995 | Crocker et al. | |
| 5,470,322 A | 11/1995 | Horzewski et al. | |
| 5,480,383 A | 1/1996 | Bagaoisan et al. | |
| 5,496,271 A | 3/1996 | Burton et al. | |
| 5,496,294 A | 3/1996 | Hergenrother et al. | |
| 5,503,263 A | 4/1996 | Watanabe | |
| 5,507,766 A | 4/1996 | Kugo et al. | |
| 5,509,910 A | 4/1996 | Lunn | |
| 5,512,051 A | 4/1996 | Wang et al. | |
| 5,514,092 A | 5/1996 | Forman et al. | |
| 5,531,715 A | 7/1996 | Engelson et al. | |
| 5,538,513 A | 7/1996 | Okajima | |
| 5,540,236 A | 7/1996 | Ginn | |
| 5,542,924 A | 8/1996 | Snoke et al. | |
| 5,542,937 A | 8/1996 | Chee et al. | |
| 5,549,552 A * | 8/1996 | Peters et al. | 604/103.1 |
| 5,549,556 A | 8/1996 | Ndondo-Lay et al. | |
| 5,554,121 A | 9/1996 | Ainsworth et al. | |
| 5,554,139 A | 9/1996 | Okajima | |
| 5,556,383 A | 9/1996 | Wang et al. | |
| 5,569,200 A | 10/1996 | Umeno et al. | |
| 5,569,218 A | 10/1996 | Berg | |
| 5,587,125 A | 12/1996 | Roychowdhury | |
| 5,605,543 A | 2/1997 | Swanson | |
| 5,643,209 A | 7/1997 | Fugoso et al. | |
| 5,645,528 A | 7/1997 | Thome | |
| 5,649,908 A | 7/1997 | Itoh | |
| 5,681,522 A | 10/1997 | Roychowdhury | |
| 5,702,439 A | 12/1997 | Keith et al. | |
| 5,716,373 A | 2/1998 | Wolvek et al. | |
| 5,725,513 A | 3/1998 | Ju et al. | |
| 5,728,063 A | 3/1998 | Preissman et al. | |
| 5,733,301 A | 3/1998 | Forman | |
| 5,743,876 A | 4/1998 | Swanson | |
| 5,746,644 A | 5/1998 | Cheetham | |
| 5,797,878 A | 8/1998 | Bleam | |
| 5,807,520 A | 9/1998 | Wang et al. | |
| 5,826,588 A | 10/1998 | Forman | |

| | | | |
|---|---|---|---|
| 5,843,050 A | 12/1998 | Jones et al. | |
| 5,843,171 A | 12/1998 | Campbell et al. | |
| 5,891,110 A | 4/1999 | Larson et al. | |
| 5,961,510 A * | 10/1999 | Fugoso et al. | 604/524 |
| 6,048,338 A | 4/2000 | Larson et al. | |
| 6,245,053 B1 | 6/2001 | Benjamin | |
| 6,475,209 B1 | 11/2002 | Larson et al. | |

FOREIGN PATENT DOCUMENTS

| | | |
|---|---|---|
| EP | 0237564 | 9/1987 |
| EP | 0277368 | 8/1988 |
| EP | 0318919 | 6/1989 |
| EP | 0448886 | 10/1991 |
| EP | 0452595 | 10/1991 |
| EP | 0452901 | 10/1991 |
| EP | 0457456 | 11/1991 |
| EP | 0485903 | 5/1992 |
| EP | 0594201 | 4/1994 |
| EP | 0669143 | 8/1995 |
| EP | 0688576 | 12/1995 |
| EP | 0718003 | 6/1996 |
| JP | 8-215312 | 8/1996 |
| WO | 93/17750 | 9/1993 |
| WO | 94/01160 | 1/1994 |
| WO | 95/09667 | 4/1995 |
| WO | 95/22367 | 8/1995 |
| WO | 96/04951 | 2/1996 |
| WO | 96/38193 | 12/1996 |
| WO | 96/39205 | 12/1996 |
| WO | 97/17889 | 5/1997 |
| WO | 00/02613 | 1/2000 |

OTHER PUBLICATIONS

Kohan, Nylon Plastics Handbook, Hanser/Gardner Publications, Inc., Cincinnati, Ohio, Copyright 1995, pp. 378-387.

Plastics Digest, Edition 15, vol. 2, 1994, p. 2-314.

TG-12X3 Centerless Grinder, one sheet, dated before Nov. 1, 2002.

* cited by examiner

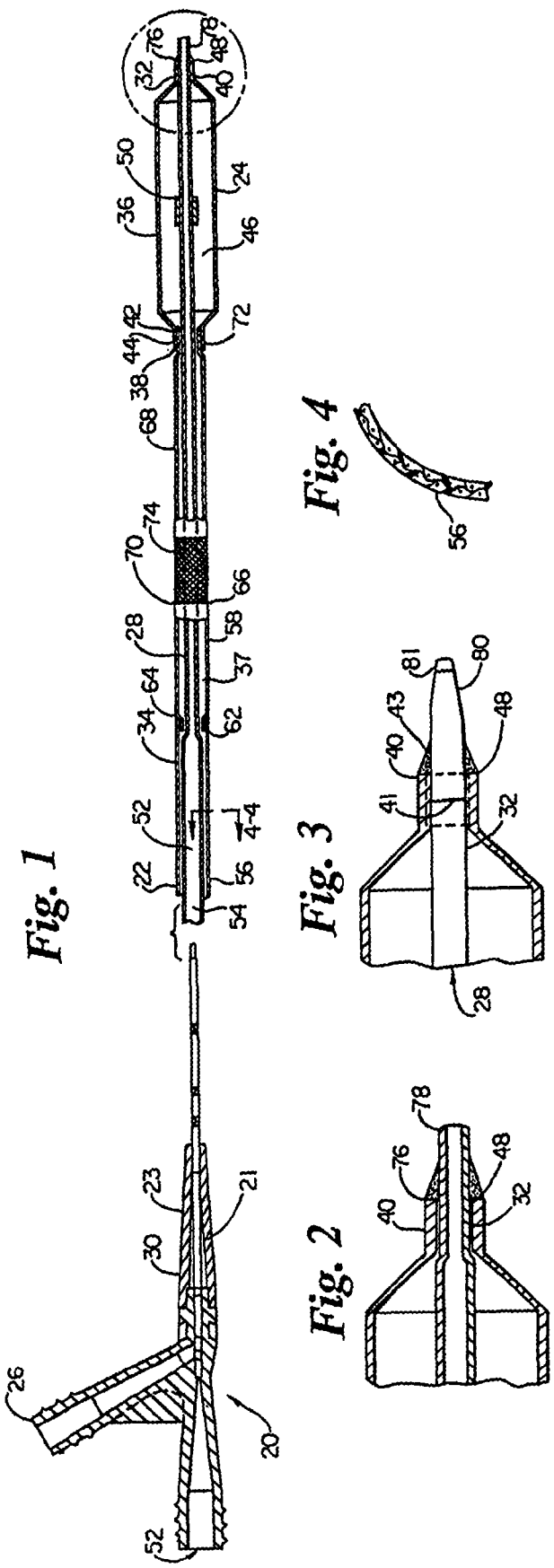

CATHETER WITH SPIRAL CUT TRANSITION MEMBER

CROSS-REFERENCE TO RELATED APPLICATIONS

This application is a continuation of U.S. application Ser. No. 11/516,062, filed Sep. 6, 2006, which is a continuation of U.S. application Ser. No. 10/285,948, filed Nov. 1, 2002, now U.S. Pat. No. 7,115,183; which is a continuation of U.S. application Ser. No. 09/534,870, filed Mar. 24, 2000, now U.S. Pat. No. 6,475,209; which is a divisional of U.S. application Ser. No. 09/241,995, filed Feb. 2, 1999, now U.S. Pat. No. 6,048,338; which is a continuation-in-part of U.S. application Ser. No. 08/950,864, filed Oct. 15, 1997, now U.S. Pat. No. 5,891,110; the entire disclosures of which are all incorporated herein by reference.

TECHNICAL FIELD

This invention relates to the field of intravascular medical devices, and more particularly, to intravascular catheters that use a relatively stiff proximal section and a more flexible distal section for improved pushability, trackability and crossability.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guide wire, possibly in combination with other intravascular devices. A typical balloon catheter has an elongate shaft with a balloon attached proximate the distal end and a manifold attached to the proximal end. In use, the balloon catheter is advanced over the guide wire such that the balloon is positioned adjacent a restriction in a diseased vessel. The balloon is then inflated and the restriction in the vessel is opened.

There are three basic types of intravascular catheters for use in such procedures including fixed-wire catheters, over-the-wire (OTW) catheters and single-operator-exchange (SOE) catheters. The general construction and use of FW, OTW and SOE catheters are all well known in the art.

Several characteristics that are important in intravascular catheters include pushability, trackability and crossability. Pushability refers to the ability to transmit force from the proximal end of the catheter to the distal end of the catheter. Trackability refers to the ability to navigate tortuous vasculature. Finally, crossability refers to the ability to navigate the balloon catheter across narrow restrictions in the vasculature.

To maximize pushability, some prior art catheters incorporate a stainless steel outer tube (also referred to as a hypotube) on the proximal shaft section and a polymeric distal shaft section. One limitation of such a construction is that hypotubing is often prone to kinking. To reduce the likelihood of kinking, some prior art catheters use a relatively stiff polymer (e.g., composite) or reinforced polymer in the proximal shaft section.

The trackability of a particular catheter design is analyzed in terms of the trackability of the distal portion of the catheter, as this portion must track the guidewire through small tortuous vessels to reach the stenosed area to be treated. A more flexible distal portion has been found to improve trackability. Therefore, to maximize pushability, the catheter should have a relatively stiff proximal section. To maximize trackability, the catheter should have a relatively flexible distal section.

A limitation of this basic structure is that kinking can occur at the joint between the relatively stiff proximal shaft section and the relatively flexible distal shaft section. To reduce the likelihood of kinking, some prior art catheters use one or more tubular sections of intermediate flexibility between the relatively stiff proximal section and the relatively flexible distal section to provide a more gradual transition in flexibility therebetween. While this approach provides some benefit, the resulting transition in flexibility is often step wise, and can still be susceptible to kinking at the junctions of the various intermediate sections. It would be desirable, therefore, to provide an intravascular catheter that has a more gradual transition in flexibility along its length.

SUMMARY OF THE INVENTION

The present invention overcomes many of the disadvantages of the prior art by providing a transition member that transitions or varies the stiffness of a catheter from a stiffer more pushable proximal section to a more flexible and trackable distal section, while reducing kinkability in the transition. The transition member preferably has a spiral cut provided therein over at least a portion of its axial length to increase the flexibility of the transition member. The pitch of the spiral cut is varied to facilitate a gradual transition in flexibility along the catheter as supported by the transition member. It is contemplated that the transition member may be used in conjunction with all types of catheters including, but not limited to, single-operator-exchange type catheters, over-the wire type catheters, and/or fixed-wire type catheters.

In one illustrative embodiment of the present invention, the transition member is used in conjunction with a catheter or other device that has a relatively stiff proximal section and a relatively flexible distal section. The junction between the stiffer proximal section and the more flexible distal section provides a transition in flexibility along the length of the catheter. Preferably, the transition member is co-axially disposed relative to the catheter shaft or other device, and is longitudinally positioned to bridge, extend across, or overlap at least part of the junction of the stiffer proximal section and the relatively flexible distal section. In a preferred embodiment, the transition member is included on a catheter having an outer tubular member which has a proximal stiff segment and a distal more flexible segment with the transition member extending both distally and proximally from the junction between these members. In a preferred over-the-wire catheter, an inner tubular member extends coaxially with the lumen of the outer tubular member and the transition member is affixed to the inner tubular member at an axial location proximate the junction in outer segments.

The flexibility of the transition member preferably increases along its length. This can be accomplished by providing a spiral cut or the like which extends through the side wall of the transition member. The spiral cut provides flexibility to the transition member, and if the pitch of the spiral cut is changed over the length, can provide a relatively smooth transition in flexibility from the relatively stiff proximal section to the relatively flexible distal section of the catheter while providing increased kink resistance. The transition member may be made from a stainless steel hypotube or other metallic tube, such as nitinol, an un-reinforced polymeric tube, a reinforced polymeric tube, or any other suitable material or element.

The transition member preferably has a first end region, an intermediate region, and a second end region, wherein only the first end region is secured to the catheter shaft. The intermediate region and the second end region are preferably left floating relative to the catheter shaft. In a preferred embodiment, the intermediate region and/or the second end region are radially spaced from the shaft when the catheter is in a substantially straight configuration, and are in engagement with at least part of the catheter shaft when the catheter is in a bent configuration.

The first end region of the transition member is secured to the shaft proximate the transition of flexibility of the shaft, with the intermediate region and the second end region extending distally therefrom. The length of the transition member is preferably sufficient so that the second end region is distal of the transition in flexibility of the shaft. Thus, like above, the transition member may bridge, extend across, or overlap at least part of the transition in flexibility of the catheter shaft.

As previously stated, in preferred embodiments, the transition member is part of or affixed to a co-axial type catheter that includes an elongate outer tube having a transition in flexibility and an elongate inner member. In one embodiment, the inner member is co-axially disposed within the lumen of the outer tube to form an annular lumen therebetween. The transition member is then preferably affixed to the inner member so that it extends coaxially therewith. The transition member extends axially from a point at or proximal of the transition in flexibility of the outer tube to a point at or distal of the transition in flexibility of the outer tube. It is contemplated that the inner member may be a inner tubular member having a guide wire lumen extending therethrough. Alternatively, it is contemplated that the inner member may be a guide wire or any other suitable device or structure. It is further recognized that the inner member can include a transition in flexibility. The transition member can be mounted on the inner member, or affixed to the outer member at an axial position so that the transition member proximal end is at or proximal to the transition flexibility and the distal end is at or distal of the transition in flexibility to provide kink resistance for the inner tubular member.

Preferably, the transition member is co-axially disposed within the annular lumen between the inner member and outer tube. It is recognized, however, that the transition member may be positioned inside the inner member (if the inner member is tubular having an inner lumen) or outside of the outer tube. The transition member is preferably positioned adjacent to at least a portion of the transition in flexibility of the catheter shaft, and is spiral cut along its length. Also, the pitch of the spiral cut may be varied at a constant or variable rate, depending on the desired flexibility characteristics of the transition member.

The outer tube may have a proximal outer section and a distal outer section joined together at a junction, with the distal outer section more flexible than the proximal outer section. The proximal end of the transition member is preferably located proximal of the junction and the distal end is preferably located distal of the junction. That is, the transition member preferably spans or bridges at least part of the transition in flexibility (i.e., junction) of the outer tube.

As previously stated, the inner member may also have a transition in flexibility. In one embodiment, the inner member has a proximal portion, an intermediate portion, and a distal portion, wherein the proximal portion has a first outer diameter, the distal portion has a second outer diameter that is smaller than the first outer diameter, and the intermediate portion has an outer diameter that tapers from the first outer diameter to the second outer diameter. The tapered intermediate portion corresponds to the transition in flexibility of the inner member.

In a preferred embodiment, the transition member is secured to or proximate to the intermediate portion of the inner member and extends distally therefrom. To help secure the transition member to the inner member, the transition member may have a proximal portion sized so that the transition member can be friction fit over a portion of the tapered portion of the inner tube. An adhesive may also be used to secure the transition member to the intermediate portion of the inner tube. In a preferred embodiment adhesive is applied proximate the proximal end of the transition member only so that the transition member distal of the adhesive is free-floating. As discussed above, the transition member may engage at least part of the inner member and outer tube when the catheter is provided in a bent configuration.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a cross-sectional view of a catheter showing a preferred embodiment of the present invention;

FIG. 2 is a partial cross-sectional view of a preferred embodiment distal tip area of the catheter of FIG. 1, illustrating the tip formed from the inner;

FIG. 3 is a partial cross-sectional view of a second preferred embodiment of distal tip area of the catheter of FIG. 1, illustrating the transition between the stiffer distal end of the inner tube and the more flexible distal tip;

FIG. 4 is a cross section view of FIG. 1 taken along line 4-4; and

DETAILED DESCRIPTION OF THE PREFERRED EMBODIMENTS

Figure 5:
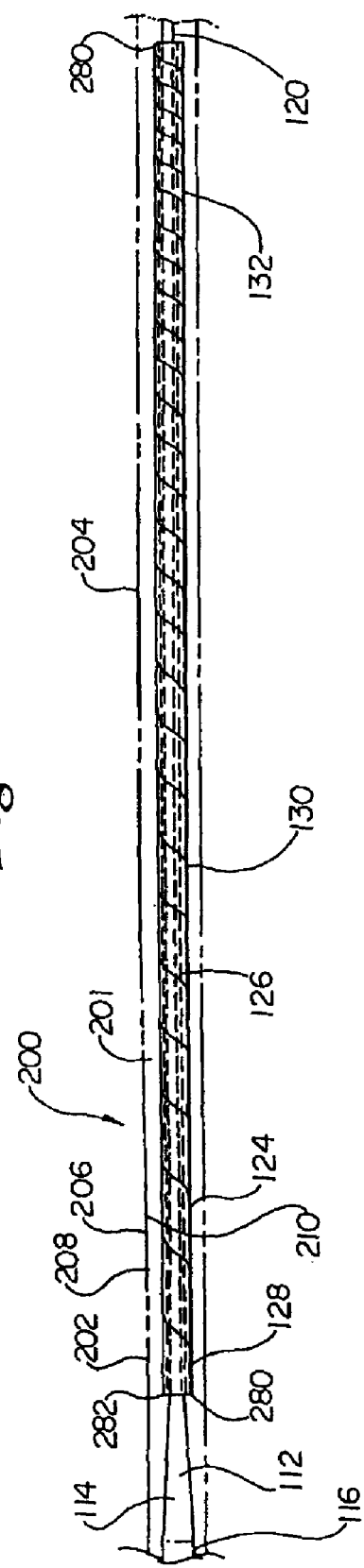
FIG. 5 is a partial cross sectional view of another embodiment of the present invention, including a spiral cut transition member bridging a transition in flexibility in the catheter shaft.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

Referring now to the drawings, FIG. 1 is a cross-sectional view of an over-the-wire balloon catheter showing a preferred embodiment of the present invention. The balloon catheter 20 includes a shaft assembly 22 and a balloon assembly 24 connected proximate its distal end. A conventional OTW-type manifold assembly 26 is connected to the proximal end of the shaft assembly 22. The shaft assembly 22 includes an inner tube 28 having a proximal end 30 and a distal end 32. The proximal end of the shaft assembly 21 extends into a manifold assembly 26 adhesively bonded to the shaft assembly 22. A polyurethane strain relief 23 is snap-fit to the manifold assembly 26, and the shaft assembly 22 extends into the manifold assembly 26 through the polyurethane strain relief 23. An outer tube 34 is co-axially disposed about the inner tube 28 to define an annular inflation lumen 37.

The balloon assembly 24 includes a balloon body portion 36 with a proximal balloon waist 38 and a distal balloon waist 40. The proximal balloon waist 38 is connected to the outer tube 34 near its distal end 42 by means of an adhesive 44, or alternatively, is thermally bonded. The distal balloon waist 40 is connected to the inner tube 28 near its distal end 32 by means of an adhesive bond 48 or a thermal bond such that the interior of the balloon 46 is in fluid communication with the annular inflation lumen 37.

A radiopaque marker band 50 is adhesively secured with cyanoacrylate to the inner tube 28 at a point underneath the balloon body 36. Alternatively, the marker band may be swaged onto the outer surface of the inner. The inner tube 28 defines a guide wire lumen 54 which provides a passage for a guide wire (not shown). The outer tube 34 defines an annular inflation lumen 37 which is in fluid communication with the interior of the balloon 46.

As previously stated, the catheter of the present invention includes an outer tube which may have multiple segments including a relatively stiff proximal outer section, a mid-shaft section of lesser stiffness, and a tapering distal outer section of the least stiffness. The progressive arrangement of more flexible materials as the catheter proceeds distally provides an optimal level of pushability and trackability to navigate tortuous vasculature. The flexibility of the sections of the outer tubular member was tested utilizing a Gurley bending resistance tester, Part No. 4171-DT, as manufactured by Precision Instruments, Troy, N.Y. The apparatus consists of a balanced pendulum or pointer which is center-pivoted and can be weighted at three points below its center. The pointer moves freely in both the left and right directions. A sample of specific size is attached to a clamp, which in turn is located in one of several positions on a motorized arm which also moves left and right. During the test, the sample is moved against the top edge of the vane, moving the pendulum until a sample bends and releases it. The test is run in two steps, first to the left and then to the right. The scale reading is measured in each direction and the results are averaged. The instrument provides a relative flexibility measurement between the components of the outer tubular member as detailed below to achieve improved trackability and pushability.

The outer tube 34 has a relatively stiff, proximal outer section 56 with a proximal end 60 and a distal end 62. The proximal outer tube may be made of nylon, a polyamide, such as DURETHAN available from Bayer, GRILAMID available from EMS-American Grilon, Inc., a DURETHAN, GRILAMID, CRISTAMID or CRISTAMID/VESTAMID blend braid or polyetheretherketone (PEEK) braid. The preferred embodiment of PEEK braid is a variable PIC tube, wherein said PIC varies from about 30 to 100 PIC to give varying flexibility over the length of the proximal outer tube. The PIC preferably varies from about 50 to about 80. The braiding material in the PEEK or DURETHAN (polymer) braid may be made from stainless steel, or Nitinol (nickel titanium alloy). This proximal outer section 56 will have an outside diameter ranging from 0.040 inches to 0.065 inches with a wall thickness ranging from 0.0026 inches to 0.0056 inches. The proximal outer section has a preferred Gurley value of about 700 to about 1300 over its length. A preferred range is about 800 to about 1200. FIG. 4 illustrates a cross section view of the proximal outer section having PEEK braid material as taken along 4-4 of FIG. 1. The PEEK braid includes an inner layer, a braid layer and an outer layer.

A midshaft section 58 with a proximal end 64 and a distal end 66 extends distally from the distal end 62 of the proximal outer section 56. The midshaft section 58 has a stiffness less than that of the proximal outer section 56. The midshaft section 58 is preferably made from a polyamide, such as CRISTAMID available from Elf Atochem, having a durometer of about 81 D. A preferred Gurley value for the midsection is about 350 to about 500, with a range of 400 to 450 preferred. This midshaft section 58 will have an outside diameter ranging from 0.040 inches to 0.045 inches with a wall thickness ranging from 0.0028 inches to 0.0044 inches.

The distal end of the proximal outer section 62 is joined to the proximal end of the midshaft section 64 with a urethane adhesive bond or a thermal weld. A distal outer section 68 having a proximal end 70 and a distal end 72 extends distally from the distal end of the midshaft section 66 to the distal end of the outer tube 44. This distal outer section 68 is more flexible or has less stiffness than both the proximal outer section 56 and the midshaft section 58. The outer diameter of the distal outer section 68 will taper from about 0.045 inches at the proximal end 70 to 0.030 inches at the distal end 72. This distal outer section 68 is made of polyether block amide (PEBAX) with a durometer of 70 D. The tapered distal outer section preferably has a Gurley value of about 70 to about 90 at its proximal end and about 15 to about 40 at its distal end. Thus, the distal end of the distal outer section 72 will exhibit less stiffness than the proximal end of the distal outer section 70. The distal end of the midshaft section 66 is joined to the proximal end of the distal outer section 70 with a urethane adhesive bond or a thermal weld.

A Nitinol braid insert 74 with a length of about 1.0" is placed within the proximal end of the distal outer section 70 to provide strain relief and reduce kinkability at the midshaft/distal outer section junction. This Nitinol braid 74 has a 0.001"×0.005" ribbon.

The inner tube 28 is made of polyethylene such as Marlex HDPE or a multilayer coextrusion with Marlex interior layer and PEBAX outer layer. At the proximal end of the inner tube 30, the inner tube 28 has an outside diameter ranging from 0.022 inches to 0.028 inches and preferably about 0.025 inches, with the inner tube 28 having an inside diameter ranging from 0.016 inches to 0.021 inches for a 0.014 inch guide wire for which this lumen is designed to be compatible with. The inner tube 28 has a wall thickness ranging from 0.0024 inches to 0.005 inches and preferably about 0.0032 inches. The outside diameter to wall thickness ratio must be sufficiently small to minimize the propensity of kinking.

As the inner tube 28 extends distally through the junction area between the distal end of the proximal outer section 62 and the proximal end of the midshaft section 64 of the outer tube 28, both the inner and outer diameters of the inner tube 28 will taper from wider diameters to narrower diameters. Likewise, at the distal end of the inner tube 32, both the inner and outer diameters of the inner tube 28 will once again taper from wider diameters to narrower diameters as the tube extends distally.

As illustrated in FIG. 2, in one preferred embodiment, a distal tip 76 is formed on the distal end of the inner tube 32 where the inner tube 28 distally tapers from a larger outer diameter to a smaller outer diameter. The distal balloon waist 40 is attached to the distal tip 76 through a urethane adhesive bond or thermal bond at a bonding area. The area just distal of the distal waist bond is backfilled with adhesive 43 to provide a smooth transition. The adhesive coating provides for improved adhesion between dissimilar substrates.

The proximal catheter shaft portion is preferably about 35 to 45 inches in length with a preferred length of 42 inches. The midshaft section, if included, can be about 1 to about 3 inches in length with a preferred length of 2 inches. The distal outer section having the most flexibility is preferably about 8 to about 12 inches in length with a preferred length of about 10 inches.

In another preferred embodiment, as shown in FIG. 3, a polyethylene, polyamide, or block copolymer such as PEBAX distal tip 80 of durometer between about 50 D and 70 D, preferably about 63 D is heat welded or bonded to the distal end of the inner tube 32 with a durometer of about 63-65 D, and the distal balloon waist 40 of the balloon is adhesively or thermally bonded to both the inner and the tip extending therefrom. As shown in FIG. 3, the joint 41 between the inner and the tip is located under the distal waist of the balloon. The outer diameter of the polyethylene distal tip 80 distally tapers from a larger outer diameter to a smaller outer diameter.

In another preferred embodiment, incorporating a soft tip as described above, the last ½ to 1 mm of the tip at its distal end is made of a different material from the tip material to form a tip extension. In particular, the last ½ to 1 mm is made from a material which is more durable relative to the softer tip material. In particular, the more durable material will resist deforming or tearing when in use, such as tracking tortuous anatomy or through a placed stent. For example, this last ½ to 1 mm may be manufactured from Marlex high-density polyethylene having a 63 D durometer which improves the integrity of the tip portion at its distal most end 81.

Referring now to FIG. 5 there is depicted a partial cross section side view of yet another embodiment of the present invention, including a spiral cut transition member that bridges or overlaps a transition in flexibility in the catheter shaft. The transition member may be used to provide a strain relief to a transition in flexibility along a length of an elongated member. More preferably, the transition member may be used to provide a strain relief to a transition in flexibility along a length of a coaxial catheter having an elongated inner member and a co-axially disposed outer member as depicted in FIG. 1. As discussed with respect to FIG. 1, numerous transitions in flexibility can be incorporated into a catheter design, such that the junction between the proximal outer 56 and the midshaft section 58 or the junction between the midshaft section 58 and the distal outer section 68. Transitions in flexibility can be included on the inner member also, such as the necking in the diameter of the inner tube 28 in FIG. 1. The transition member of the present invention can be used in conjunction with any such transition in flexibility. FIG. 5 is illustrative of such uses.

The illustrative catheter shaft of FIG. 5 includes an inner member 112 that has a proximal portion 116, an intermediate portion 114, and a distal portion 120. It is contemplated that the inner member 112 may be a guide wire, an inner tubular member, or any other suitable device or structure. In the embodiment shown, the proximal portion 116 has a first outer diameter, and the distal portion 120 has a second outer diameter that is smaller than the first outer diameter. The intermediate portion 114 has an outer diameter that tapers from the first outer diameter to the second outer diameter. The tapered intermediate portion 114 provides a transition in flexibility from the stiffer proximal portion 116 to the more flexible distal portion 120 of the inner member 112. Preferably, the inner member 112 is an inner tubular member having a guide wire lumen extending therethrough, and is preferably made from a polymeric material, such as polyethylene, or a multi-layer extrusion having a polyethylene inner and PEBAX outer layer. It is recognized that the tube may be un-reinforced polymeric tube, a reinforced polymeric tube, or any other suitable material or element.

A transition member 124 may be used in conjunction with the inner member 112, or in conjunction with the inner member 112 and the outer member 200, as more fully described below. The transition member 124 is shown co-axially disposed relative to the inner member 112, and longitudinally positioned to bridge or overlap at least part of the transition in flexibility of the inner member 112. In preferred embodiments, the transition member has a length of about 2 inches. This length can, however, be varied for specific applications, with preferred lengths of about 0.5 inches to about 4 inches, more preferably, about 1.5 inches to about 2.5 inches.

To help provide a transition in flexibility, the transition member 124 has a spiral cut 126 or the like in the side wall thereof. The spiral cut preferably extends through the side wall of the transition member 124. The pitch of the spiral cut 126 may be varied along the length of the transition member 124 to provide a relatively smooth transition from the relatively stiff proximal portion 116 to the more flexible distal portion 120 of the inner member 112. The pitch may be varied at a constant or variable rate, depending on the desired flexibility characteristics of the transition member 124. The pitch may be held constant over a portion of the length of the transition member 124 and varied over other portions of the length to achieve desired flexibility for a particular use. In a preferred embodiment, the spiral cut has a pitch at the proximal end of about 0.11 inches, a pitch in the distal end of about 0.03 inches, and a constant rate of change over its length. it is recognized that pitch can be varied depending upon a particular application with a preferred proximal end pitch of up to 0.3 inches and a distal end pitch of down to 0.01 inches. The pitch is defined herein as the axial distance between an adjacent (360°) spiral cut. In general, pitch is selected so that the flexibility of the transition member in combination with shaft provides a smooth transition in flexibility with no abrupt changes. Spiral cut 126 is preferably formed in the transition member 124 using a laser.

The transition member 112 has a first end region 128, an intermediate region 130, and a second end region 132, wherein only the first end region 128 is secured to the inner member 112. The intermediate region 130 and the second end region 132 are left floating relative to the inner member 112. The intermediate region 130 and the second end region 132 are preferably spaced from the inner member 112 when the catheter is in a substantially straight configuration, but become in contact with at least parts of the inner member 112 when the catheter is in a bent configuration.

It is contemplated that the first end region 128, the second end region 132, and/or the intermediate region 130 may be secured to the inner member 112. It is also contemplated that there may be a space between the inner member 112 and the first end region 128, the second end region 132 and/or the intermediate region 130. It is also contemplated that there may not be a space between the inner member 12 and the first end region 128, the second end region 132 and/or the intermediate region 130.

The first end region 128 of the transition member 124 may be secured to the inner member 112 proximate the transition in flexibility of the inner member 112, with the intermediate region 130 and the second end region 132 extending distally therefrom without attachment to the inner so that these portions are free floating and can flex without restraint. The length of the transition member 124 is preferably selected so that the second end region 132 extends distal of the transition in flexibility in the inner member 112. In this configuration, the transition member 124 bridges or overlaps at least part of the transition in flexibility of the inner member 112. Preferably, the transition member 124 is formed from a heat treated stainless steel hypotube, but could be manufactured from another alloy, such as nitinol, or a polymeric material.

As shown in FIG. 5, the catheter shaft may also include an outer tube 200 having a lumen 201 extending therethrough. The inner tube 112 and outer tube 200 are preferably co-axially disposed forming the annular lumen 201 therebetween. The outer tube 200 has a relatively stiff proximal outer section 202 and a relatively flexible distal outer section 204. The progressive arrangement of more flexible materials as the catheter proceeds distally provides an optimal level of pushability and trackability to navigate tortuous vasculature.

The proximal outer tube 202 may correspond to the proximal outer tube 56 of the embodiment shown in FIG. 1. Thus, the proximal outer tube 202 may be made of nylon, a polyamide, such as DURETHAN available from Bayer, a DURETHAN braid, polyetheretherketone (PEEK) braid or any other suitable material or combination of materials. Alternatively, the proximal outer tube 202 may correspond to the midshaft section 58 of the embodiment shown in FIG. 1. Thus, the proximal outer tube 202 may be made from a polyamide, such as CRISTAMID available from Elf Atochem, having a durometer of about 81 D, and may have an outside diameter ranging from 0.040 inches to 0.045 inches with a wall thickness ranging from 0.0028 inches to 0.0044 inches.

The distal outer section 204 may have a proximal end 206 that extends distally from the distal end 208 of the proximal outer section 202. The distal outer section 204 preferably has a stiffness that is less than that of the proximal outer section 202. The distal outer section 204 may correspond to the midshaft section 58 of the embodiment shown in FIG. 1. Thus, the distal outer section 204 may be made from a polyamide, such as CRISTAMID available from Elf Atochem, having a durometer of about 81 D, with an outside diameter ranging from 0.040 inches to 0.045 inches with a wall thickness ranging from 0.0028 inches to 0.0044 inches. Alternatively, the distal outer section 204 may correspond to the distal outer section 68 of the embodiment shown in FIG. 1. Thus, the distal outer section 204 may be made from a polyether block amide (PEBAX) having a durometer of about 70 D.

The distal end 208 of the proximal outer section 202 is preferably joined to the proximal end 206 of the distal outer section 204 at a junction 210 using a urethane adhesive bond or a thermal weld. Because the proximal outer section 202 is preferably stiffer than the distal outer section 204, there is a transition in flexibility in the outer tube 200 at junction 210. This transition in flexibility may be rather abrupt, as provided by an adhesive lap-joint or a thermal butt-joint, or may be more gradual, as provided by a heat flow process or an interrupted layer extrusion process. The proximal end of the transition member 124 may be located proximal of the junction 210 in the outer tube 200, and the distal end may be located distal of the junction 210. Thus, the transition member 124 may span or bridge at least part of the transition in flexibility (i.e. junction 210) of the outer tube 200.

The transition member 124 is preferably co-axially disposed within the annular lumen between the inner member 112 and the outer tube 200. It is recognized, however, that the transition member may be positioned inside the inner member 112 (if the inner member 112 is tubular having an inner lumen) or outside of the outer tube 200. The transition member 124 is preferably longitudinally positioned adjacent to at least a portion of the transition in flexibility of the inner member 112, the outer tube 200, or both.

Like above, the transition member may be secured to the intermediate portion 114 of the inner member 112. To help secure the transition member 124 to the inner member 112, the proximal portion may be sized so that the transition member 124 can be friction fit over the intermediate portion 114. An adhesive may also be used to secure the transition member 124 to the intermediate portion 114 of the inner tube 112.

Finally, a radius cut 280 may be provided in the transition member 124 to remove any sharp edges that may exists at the proximal end and distal end of transition member 124. It is recognized that spiral cut 126 may result in a sharp edge or point at the proximal end 282 or termination of the spiral cut of the transition member 124. This sharp edge or point may engage the outer tube 200 when the catheter is bent. To help reduce any damage that may result, a radius cut 280 may be provided to round the edge proximal end 282. This may be accomplished by cutting, grinding, filing or any other means that provides a smoother less obtrusive edge to the proximal end of the end coil 282. For similar reasons, a radius cut may also be provided at the distal end of the transition member 112.

Having thus described the preferred embodiments of the present invention, those of skill in the art will readily appreciate that yet other embodiments may be made and used within the scope of the claims hereto attached.

What is claimed is:

1. A catheter, comprising:
   an outer shaft having a proximal outer section having a distal end, a midshaft section having a distal end and having a proximal end attached to the distal end of the proximal outer section, and a distal outer section having a proximal end attached to the distal end of the midshaft section;
   wherein the proximal outer section has a first stiffness;
   wherein the midshaft section has a second stiffness that is less than the first stiffness;
   wherein the distal outer section has a third stiffness that is less than the second stiffness;
   an insert disposed within the outer shaft and extending from a first position adjacent to the distal end of the midshaft section to a second position adjacent to the proximal end of the distal outer section, the insert being configured to provide a smooth transition in flexibility between the midshaft section and the distal outer section;
   an inner shaft disposed within the outer shaft, the inner shaft having a distal tip attached thereto at a joint;
   a spiral cut transition member disposed about the inner shaft, wherein the spiral cut transition member includes a spiral cut with a pitch that varies along the length of the spiral cut transition member; and
   a balloon having a proximal waist attached to the outer shaft and a distal waist positioned about the joint.

2. The catheter of claim 1, wherein the proximal outer section includes a braid.

3. The catheter of claim 1, wherein the insert includes a braid.

4. The catheter of claim 3, wherein the insert includes a nickel-titanium alloy.

5. The catheter of claim 1, wherein the inner tube includes one or more tapers.

6. The catheter of claim 1, wherein a coating is disposed adjacent to the distal waist to provide a smooth transition between the distal waist and the inner shaft.

7. The catheter of claim 6, wherein the coating includes an adhesive.

8. The catheter of claim 1, wherein the inner shaft includes a radiopaque marker band.

9. A catheter, comprising:
   an outer shaft having a proximal outer section having a distal end, a midshaft section having a distal end and having proximal end attached to the distal end of the proximal outer section, and a distal outer section having a proximal end attached to the distal end of the midshaft section;
   wherein the proximal outer section has a first stiffness;
   wherein the midshaft section has a second stiffness that is less than the first stiffness;
   wherein the distal outer section has a third stiffness that is less than the second stiffness;
   an inner shaft disposed within the outer shaft, the inner shaft having a proximal inner section, an inner midshaft section, and a distal inner section;
   a spiral cut transition member disposed about the inner shaft, wherein the spiral cut transition member includes a spiral cut with a pitch that varies along the length of the spiral cut transition member;
   wherein the proximal inner section has a first outer diameter;
   wherein the inner midshaft section has a second outer diameter less than the first outer diameter;
   wherein the distal inner section has a third outer diameter less than the second outer diameter; and
   a balloon having a proximal waist attached to the outer shaft and a distal waist attached to the inner shaft.

10. The catheter of claim 9, wherein the inner shaft has a distal tip attached thereto at a joint.

11. The catheter of claim 10, wherein the distal waist of the balloon is disposed about the joint.

12. The catheter of claim 9, wherein the proximal outer section includes a braid.

13. The catheter of claim 9, wherein the proximal inner section has a first inner diameter, wherein the inner midshaft section has a second inner diameter less than the first inner diameter, and wherein the distal inner section has a third inner diameter less than the second inner diameter.

14. The catheter of claim 9, wherein a coating is disposed adjacent to the distal waist to provide a smooth transition between the distal waist and the inner shaft.

15. The catheter of claim 14, wherein the coating includes an adhesive.

16. The catheter of claim 9, wherein the inner shaft includes a radiopaque marker band.

17. The catheter of claim 9, wherein an insert is disposed within the outer shaft and extends between the midshaft section and the distal outer section.

18. A catheter, comprising:
   an outer shaft having a proximal outer section having a distal end, a midshaft section having a distal end and having a proximal end attached to the distal end of the proximal outer section, and a distal outer section having a proximal end attached to the distal end of the midshaft section;
   wherein the proximal outer section has a first stiffness;
   wherein the midshaft section has a second stiffness that is less than the first stiffness;
   wherein the distal outer section has a third stiffness that is less than the second stiffness;
   an insert disposed within the outer shaft and extending from a position adjacent to the distal end of the midshaft section to a second position adjacent to the proximal end of the distal outer section, the insert being configured to provide a smooth transition in flexibility between the midshaft section and the distal outer section;
   an inner shaft disposed within the outer shaft, the inner shaft having a proximal inner section, a inner midshaft section, and a distal inner section;
   wherein the proximal inner section has a first outer diameter;
   wherein the inner midshaft section has a second outer diameter less than the first outer diameter;
   wherein the distal inner section has a third outer diameter less than the second outer diameter;
   a spiral cut transition tube disposed about the inner shaft, wherein the spiral cut transition tube includes a spiral cut with a pitch that varies along the length of the spiral cut transition tube; and
   a balloon having a proximal waist attached to the outer shaft and a distal waist attached to the inner shaft.

* * * * *